(12) United States Patent
Mackool

(10) Patent No.: US 7,172,578 B2
(45) Date of Patent: Feb. 6, 2007

(54) STERILE TUBING SHEATH

(75) Inventor: Richard J. Mackool, Astoria, NY (US)

(73) Assignee: Alcon, Inc., Hünenberg (CH)

( * ) Notice: Subject to any disclaimer, the term of this patent is extended or adjusted under 35 U.S.C. 154(b) by 99 days.

(21) Appl. No.: 10/825,046

(22) Filed: Apr. 15, 2004

(65) Prior Publication Data

US 2005/0234395 A1 Oct. 20, 2005

(51) Int. Cl.
*A61M 1/00* (2006.01)

(52) U.S. Cl. .......................... 604/181; 604/35
(58) Field of Classification Search ............... 604/118, 604/181, 171, 173, 22, 35; 433/91, 116
See application file for complete search history.

(56) References Cited

U.S. PATENT DOCUMENTS

| | | | | |
|---|---|---|---|---|
| 633,805 | A * | 9/1899 | Chandler | 604/38 |
| 3,902,500 | A * | 9/1975 | Dryden | 128/207.14 |
| 4,014,342 | A * | 3/1977 | Staub et al. | 606/170 |
| 4,327,735 | A * | 5/1982 | Hampson | 604/171 |
| 4,810,194 | A * | 3/1989 | Snedden | 433/91 |
| 5,242,398 | A * | 9/1993 | Knoll et al. | 604/103.05 |
| 5,301,657 | A | 4/1994 | Lafferty et al. | |
| 5,364,342 | A | 11/1994 | Beuchat et al. | |
| 5,697,887 | A | 12/1997 | Yabe et al. | |
| 5,741,226 | A * | 4/1998 | Strukel et al. | 604/35 |
| 6,280,449 | B1 * | 8/2001 | Blake | 606/107 |
| 6,282,442 | B1 * | 8/2001 | DeStefano et al. | 604/21 |
| 6,524,251 | B2 * | 2/2003 | Rabiner et al. | 600/439 |
| 6,610,033 | B1 * | 8/2003 | Melanson et al. | 604/181 |
| 6,641,566 | B2 * | 11/2003 | Douglas et al. | 604/218 |
| 6,740,074 | B2 * | 5/2004 | Morgan et al. | 604/540 |
| 6,960,182 | B2 * | 11/2005 | Moutafis et al. | 604/43 |
| 2003/0004455 | A1 | 1/2003 | Kadziauskas et al. | |
| 2004/0176727 | A1 * | 9/2004 | Shekalim | 604/181 |

FOREIGN PATENT DOCUMENTS

| EP | 0 570 255 A | | 11/1993 |
|---|---|---|---|
| EP | 570255 A1 | * | 11/1993 |

OTHER PUBLICATIONS

International Search Report mailed Jun. 29, 2005 in PCT/US2005/007466.

Written Opinion of the International Searching Authority in PCT/US2005/007466.

* cited by examiner

*Primary Examiner*—Melissa McCorkle
(74) *Attorney, Agent, or Firm*—Hess Patent Law Firm; Robert J. Hess

(57) ABSTRACT

A flexible sheath is attached to an end of a rigid extension tube. The other end of the rigid extension tube is connected with a surgical handpiece. Two flexible sheaths may be used—one as a barrier against contamination of aspiration tubing and the other as a barrier against contamination of irrigation tubing. This is effected by securing two rigid extension tubes between the surgical handpiece and an associated one of the aspiration and irrigation tubings. Each flexible sheath is collapsible and expandable so they may be expanded from a collapsed condition over the associated aspiration or irrigation tubings and secured in the expanded condition. The aspiration and/or irrigation tubings are connected to a cassette of a surgical pack.

6 Claims, 2 Drawing Sheets

STERILE TUBING SHEATH

BACKGROUND OF THE INVENTION

The present invention relates to a sterile tubing sheath as part of a sterilized barrier apparatus and to a method of forming a sterilized barrier for an aspiration tube used with a surgical handpiece in ocular surgery procedures.

DISCUSSION OF RELATED ART

During various types of surgical procedures, one or more sterile, hollow tubings may be used to transport fluid to the eye and to transport fluid, tissue, blood, etc. from the eye. Such surgical procedures are exemplified by certain ocular procedures such as cataract removal and vitrectomy operations.

Such sterile, hollow tubings are typically sold in combination with a "cassette", which is a collection vehicle into which the removed fluid, tissue, etc. is deposited. Alcon Laboratories, Inc., Alcon Universal Ltd, Alcon Surgical, Inc., Alcon Manufacturing, Ltd. or Alcon, Inc. is a supplier of such a cassette.

The combination of one or more sterile, hollow tubings and the cassette is typically referred to as a surgical pack. The surgical pack can be expensive and requires a certain amount of time to install in an instrument used for the accomplishment of the desired surgical procedure The external surface of the hollow tubings may become contaminated from handling or from exposure to the patient during the surgical operation. Currently, these surgical packs are generally used only once and then disposed, which is obviously wasteful of the surgical packs. Occasionally, the tubing is removed, cleaned and sterilized and then re-used. However, such removing, cleaning and sterilizing procedures are labor intensive of staff time and costly as concerns use of the sterilizing agents. Such procedures result in a relatively inefficient use of staff time and create downtime in use of the surgical packs and thus inefficient use of them until the sterilizing process is over and the packs are once again installed into position.

It would be desirable to re-use the surgical packs safely for operations involving different patients without introducing a risk of contamination to any of the patients.

BRIEF SUMMARY OF THE INVENTION

One aspect of the invention resides in a sterilized barrier and method of forming a sterilized barrier for an aspiration tubing and an irrigation (infusion) tubing to a surgical handpiece.

BRIEF DESCRIPTION OF THE DRAWINGS

For a better understanding of the present invention, reference is made to the following description and accompanying drawings, while the scope of the invention is set forth in the appended claims.

DETAILED DESCRIPTION OF THE INVENTION

An intent of the invention is that after completion of a surgical procedure, tubings, cassette, etc. are left in place. That is, they are permitted to remain attached to the instrument console 10 (FIG. 1).

Figure 1:
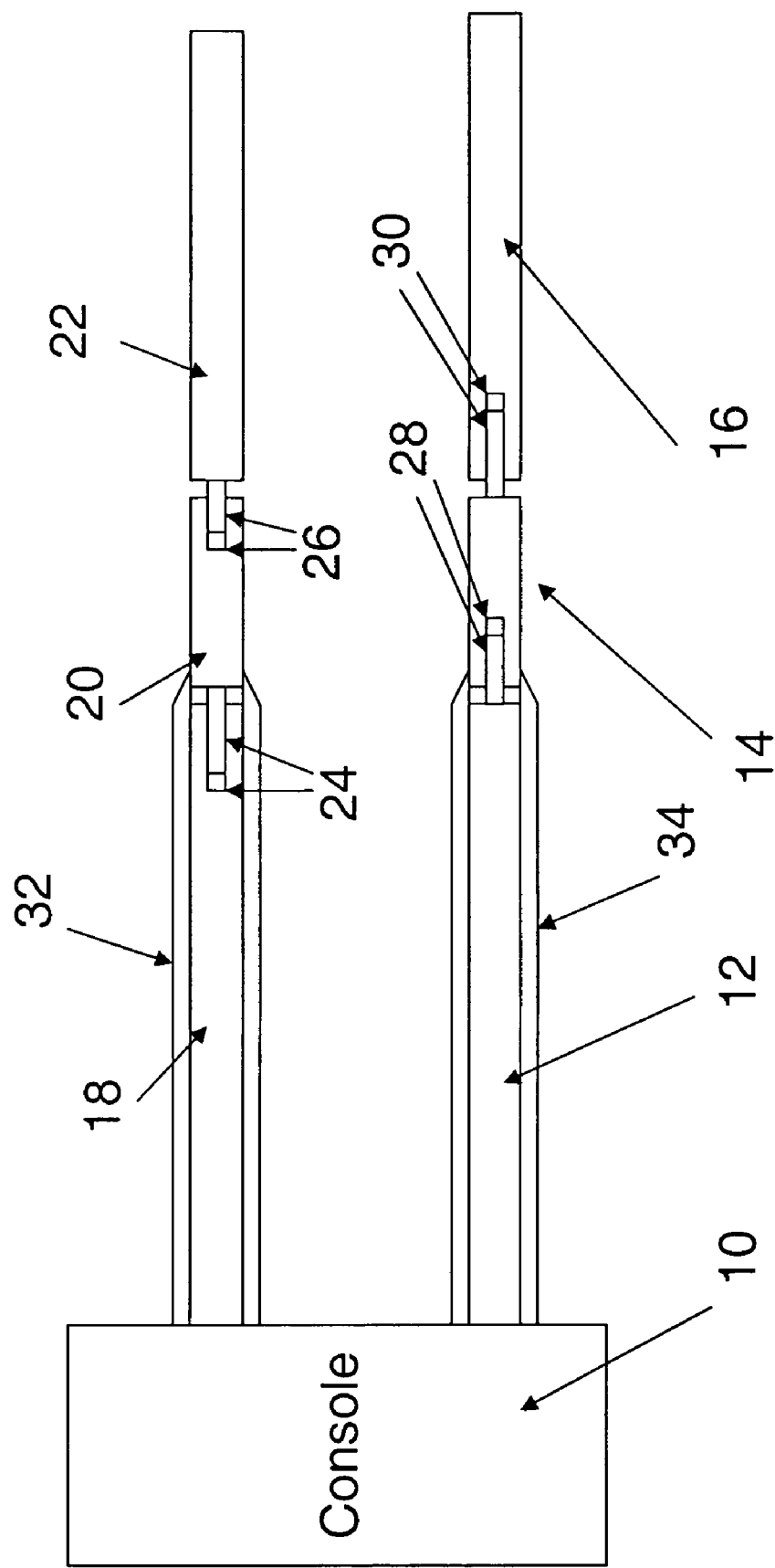
FIG. 1 is a schematic representation of a surgical pack employing a sheath of the present invention, with the sheath shown in an expanded condition.

As shown in FIG. 1, an infusion or irrigation tubing 12 extends from the console 10. A small extension tube 14 is preferably rigid and constructed so as to not significantly alter the inner diameter of the lumen of the tubing 12. The small extension tube 14 has a proximal end attached to the distal end of the infusion or irrigation tubing 12 using conventional sterile technique. The distal end of the small extension tube 14 is in turn connected to a metallic tubing 16 of a surgical handpiece.

An aspiration tubing 18 extends from the console 10. A further small extension tube 20, which is also preferably rigid, is constructed as well so as to not to significantly alter the inner diameter of the lumen of the aspiration tubing 18, and is likewise attached using conventional sterile technique. The further small extension tube 20 has a proximal end attached to the distal end of the aspiration tubing 18. The distal end of the further small extension tube 20 is in turn connected to a further metallic tubing 22 of the surgical handpiece.

Male and female connectors 24 engage each other in a mating manner to connect the aspiration tubing 18 and the further small extension tube 20 together. Male and female connectors 26 engage each other in a mating manner to connect the further small extension tube 20 with the metallic tubing 22. Also, male and female connectors 28 engage each other in a mating manner to connect the irrigation tubing 12 to the small extension tube 14. Male and female connectors 30 engage each other in a mating manner to connect the small extension tube 14 to the metallic tubing 16. FIG. 1 shows the connectors 28, 30 almost fully mated. Once fully mated, the connectors 28, 30 may have their surfaces configured to engage each other in a manner that retains their mated state to avoid inadvertent separation.

Figure 2:
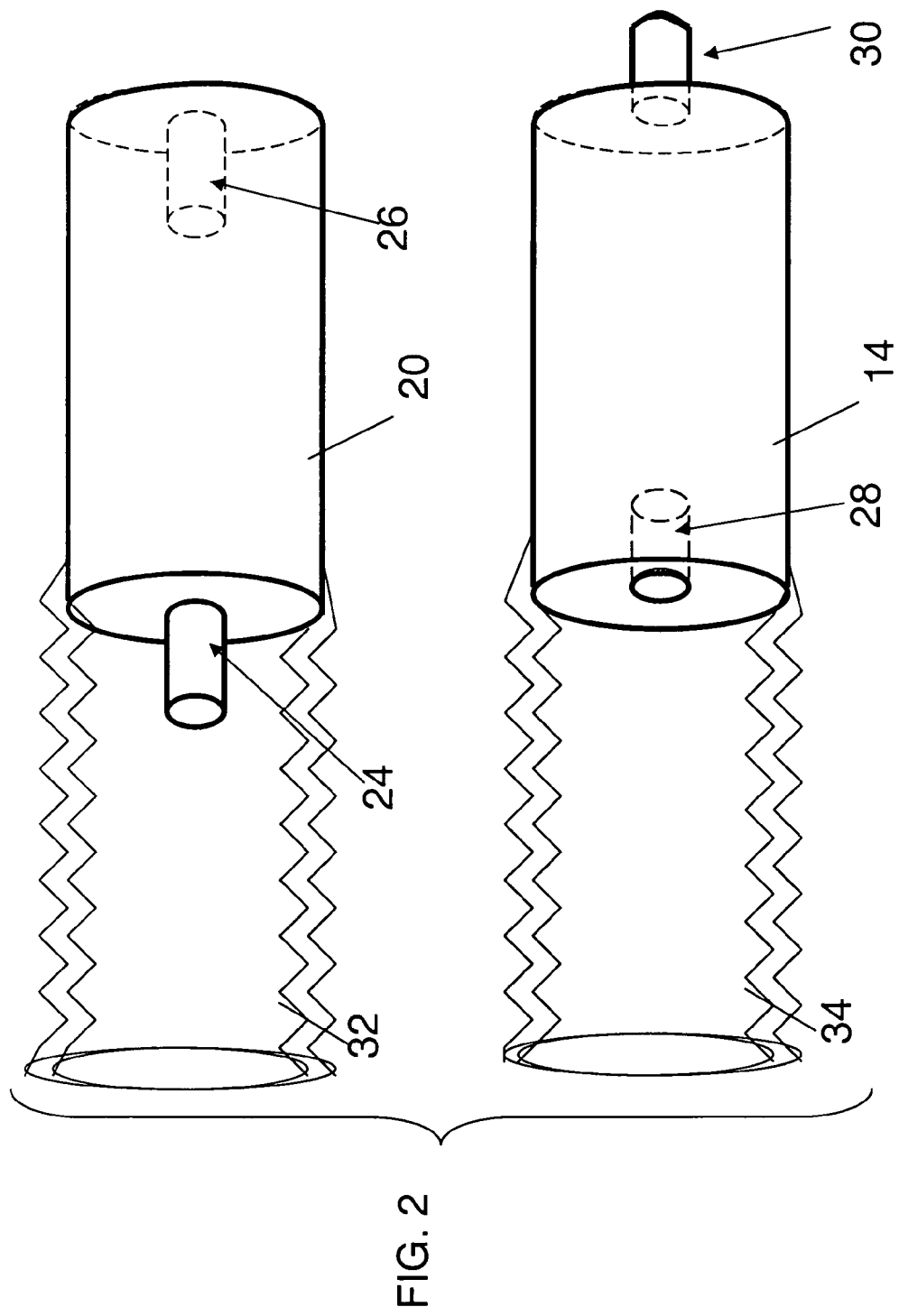
FIG. 2 is a schematic representation of the sheaths and rigid extension tubes of FIG. 1 but in a collapsed condition.

The small extension tube 14 and the further small extension tube 20 may each be a rigid tubing attachment that has attached to it in any conventional manner, such as with an adhesive, a respective, soft sheath 32, 34. The sheaths 32, 24 may be pre-rolled or collapsed in accordion fashion (FIG. 2) and expandable to form a structure that may be symmetric, such as tubular (FIG. 1). Each sheath 32, 34 is hollow and open at one end to enable being pulled over the associated (irrigation or aspiration) tubing as applicable and toward the surgical instrument console. The open end of the sheath 32, 24 is then attached either to a port of the console or to an end of the associated tubing in relative close proximity to the port. The attachment of the sheath 32, 34 to the port or to the end of the associated tubing may be effected in any conventional manner, such as with an adhesive. The sheaths each present a completely sterile external surface placed over the tubing to serve a sterilized barrier.

Typically, there are two tubings attached to the console, i.e, the irrigation tubing 12 and the aspiration tubing 18. The distal end of each of these tubings differ from each other in configuration to avoid confusion (one is male and the other is female). In accordance with the invention, each of these distal ends is attached to its own small extension tube, which in turn is attached to a respective metallic tubing 16, 22 of the sterilized surgical handpiece. The handpiece may be an ultrasonic instrument, cutting instrument, illuminated irrigating instrument, etc.

The aspiration tubing 18, which is tubing that leaves the surgical site, could be subjected to a sterilization procedure by internally irrigating prior to the application of the sheath 32. This could be done by the inserting the aspiration tubing into a sterile container of preparatory fluid, which is then aspirated to remove fluid within it that remained from the previous surgical procedure. Alternatively, at the conclusion of the previous surgical procedure, the instrument's pump could be permitted to run with the surgical instrument in atmospheric air. Fluid within the aspiration tubing would thereby be completely removed prior to attachment of the sterile extension and surrounding sheath.

The irrigation tubing 12, which is tubing that is used to deliver fluid to the eye, does not need to be cleared of fluid because its contents are sterile and have not entered a surgical field. However, after each use, this tubing could be cleared of fluid by simple gravitational flow if desired.

Conventionally, as soon as the aspiration or irrigation tubing is exposed to a patient or a gloved hands of a technician or surgeon, such tubing is considered to be contaminated and thus could not be re-used during a subsequent operation without proper sterilization.

In accordance with the intention, however, only the sheaths and the small extension tubes would become contaminated upon exposure to the patient or the gloved hands of the technician or surgeon. Thus, only the sheaths and the small extension tubes would need to be discarded after each surgical procedure. The aspiration and irrigation tubings that are shrouded by the sheaths and the cassette to which the tubings are attached would not need to be discarded but rather could be reused, after implementing the previously mentioned sterilization technique on the aspiration tubing and possibly allowing for gravitational flow for the irrigation tubing.

While the foregoing description and drawings represent embodiments of the present invention, it will be understood that various changes and modifications may be made without departing from the scope of the present invention.

What is claimed is:

1. A sterilized barrier apparatus, comprising:
   a sterile, tubular sheath that is configured to displace between expanded and collapsed conditions;
   a hollow extension tube secured to a distal end of the sterile, tubular sheath; and
   an instrument console with a surgical pack that includes an aspiration tube having a distal end to which is attached the hollow extension tube, the aspiration tube projecting from the instrument console, the sterile, tubular sheath being arranged to contain the aspiration tube within confines of the sterile, tubular sheath between the hollow extension tube and the instrument console and thereby serve as sterilized barrier against exposure of the aspiration tube to contamination, the sterile tubular sheath being secured to either an end of the aspiration tube in close proximity to the port, or the port of the console.

2. A sterilized barrier apparatus of claim 1, wherein the surgical pack includes a cassette arranged to receive contents of the aspiration tube that are being aspirated, the aspiration tube having a proximal end closer to the cassette than the distal end of the aspiration tube, a location where the sterile, tubular sheath is secured to the aspiration tube being closer to the proximal end than to the distal end of the aspiration tube.

3. A sterilized barrier apparatus of claim 1, wherein the instrument console has a suction pump that, when activated, suctions the aspiration tube.

4. A sterilized barrier apparatus of claim 1, further comprising a surgical handpiece attached to the distal end of the aspiration tube.

5. A sterilized barrier apparatus of claim 1, wherein a surgical handpiece is attached to a distal end of the hollow, extension tube.

6. A sterilized barrier apparatus of claim 1, wherein the sterile, tubular sheath is configured so as to be collapsible into the collapsed condition in an accordion fashion.

* * * * *